(12) United States Patent
Saitoh et al.

(10) Patent No.: US 10,004,915 B2
(45) Date of Patent: Jun. 26, 2018

(54) TRANSCRANIAL MAGNETIC STIMULATION SYSTEM

(71) Applicants: TEIJIN PHARMA LIMITED, Chiyoda-ku, Tokyo (JP); OSAKA UNIVERSITY, Suita-shi, Osaka (JP)

(72) Inventors: Youichi Saitoh, Suita (JP); Kenji Tojo, Hino (JP); Atsushi Asahina, Hino (JP)

(73) Assignees: Teijin Pharma Limited, Tokyo (JP); OSAKA UNIVERSITY, Osaka (JP)

( * ) Notice: Subject to any disclaimer, the term of this patent is extended or adjusted under 35 U.S.C. 154(b) by 360 days.

(21) Appl. No.: 14/353,559

(22) PCT Filed: Oct. 24, 2012

(86) PCT No.: PCT/JP2012/077524
§ 371 (c)(1),
(2) Date: Jun. 26, 2014

(87) PCT Pub. No.: WO2013/062022
PCT Pub. Date: May 2, 2013

(65) Prior Publication Data
US 2015/0038768 A1 Feb. 5, 2015

(30) Foreign Application Priority Data
Oct. 24, 2011 (JP) .................................. 2011-232883

(51) Int. Cl.
*A61N 2/02* (2006.01)
*A61N 2/00* (2006.01)

(52) U.S. Cl.
CPC .............. *A61N 2/02* (2013.01); *A61N 2/006* (2013.01)

(58) Field of Classification Search
CPC . A61B 19/5202; A61B 19/5212; A61B 19/54; A61B 19/5445; A61B 19/20; A61N 2/006; A61N 2/02
(Continued)

(56) References Cited

U.S. PATENT DOCUMENTS 3,116,365 A * 12/1963 Prescott ................. H04N 7/142
348/14.16
2003/0073899 A1 4/2003 Ruohonen et al.
(Continued)

FOREIGN PATENT DOCUMENTS

EP 2008687 A1 12/2008
EP 2444119 A1 4/2012
(Continued)

OTHER PUBLICATIONS

Lebosse, Cyrille, Pierre Renaud, Bernard Bayle, Michel De Mathelin, Olivier Piccin, and Jack Foucher. "A Robotic System for Automated Image-guided Transcranial Magnetic Stimulation." 2007 IEEE/NIH Life Science Systems and Applications Workshop (2007): 55-58. Web. Feb. 18, 2016.*
(Continued)

*Primary Examiner* — Navin Natnithithadha
*Assistant Examiner* — Sunita Reddy
(74) *Attorney, Agent, or Firm* — Sughrue Mion, PLLC

(57) ABSTRACT

A compact and economical transcranial magnetic stimulation system is provided which allows patient to carry out transcranial magnetic stimulation therapy routinely and repeatedly in, for example, his or her house or a neighborhood primary-care medical facility. The system (1) has a magnetic field generating means for generating a magnetic field to be used for providing magnetic stimulation to a specific part of the patient's head. The magnetic field generating means has a magnetic coil (2) for generating a
(Continued)

variable magnetic field, a holder (10) for holding the magnetic coil (2), cameras (150*a*) and another for recognizing respective reference markings (24) or specific portions of ears of the patient M (tragi (24)), and laser beam oscillators (160*a*) and another. According to the system, the coil (2) is set in a proper posture with respect to the specific part of the patient by aligning the optical axes of the cameras (150*a*) and other and the laser beam oscillators (160*a*) and other with respective tragi (24).

16 Claims, 7 Drawing Sheets

(58) Field of Classification Search
USPC .......................................... 600/13, 424, 426
See application file for complete search history.

(56) References Cited

U.S. PATENT DOCUMENTS

| | | | |
|---|---|---|---|
| 2004/0039279 A1 | 2/2004 | Ruohonen | |
| 2005/0025353 A1 | 2/2005 | Kaneko et al. | |
| 2005/0148808 A1* | 7/2005 | Cameron | A61G 15/125 600/13 |
| 2005/0193451 A1 | 9/2005 | Quistgaard et al. | |
| 2005/0234286 A1 | 10/2005 | Riehl et al. | |
| 2006/0122496 A1 | 6/2006 | George et al. | |
| 2006/0161039 A1* | 7/2006 | Juliana | A61N 2/006 600/9 |
| 2006/0287566 A1* | 12/2006 | Zangen | A61N 2/02 600/15 |
| 2007/0078466 A1* | 4/2007 | Bodduluri | A61B 17/32053 606/133 |
| 2008/0139871 A1 | 6/2008 | Muntermann | |
| 2008/0161716 A1 | 6/2008 | Livne et al. | |
| 2009/0187062 A1 | 7/2009 | Saitoh | |
| 2009/0216067 A1 | 8/2009 | Lebosse | |
| 2009/0227830 A1 | 9/2009 | Pillutla et al. | |
| 2010/0036191 A1* | 2/2010 | Walter | A61N 2/006 600/14 |
| 2010/0234871 A1* | 9/2010 | Qureshi | A61F 2/10 606/187 |
| 2011/0230701 A1* | 9/2011 | Simon | A61N 1/36021 600/9 |
| 2012/0157752 A1 | 6/2012 | Nishikawa et al. | |
| 2014/0179981 A1* | 6/2014 | Katz | A61N 2/006 600/15 |

FOREIGN PATENT DOCUMENTS

| | | |
|---|---|---|
| JP | 1049218 A | 2/1998 |
| JP | 11-197259 A | 7/1999 |
| JP | 2003-180649 A | 7/2003 |
| JP | 2004-000636 A | 1/2004 |
| JP | 2006102406 A | 4/2006 |
| JP | 2006-320425 A | 11/2006 |
| JP | 2007520290 A | 7/2007 |
| JP | 2008505662 A | 2/2008 |
| JP | 2008-528108 A | 7/2008 |
| JP | 2008532722 A | 8/2008 |
| JP | 2009-509671 A | 3/2009 |
| JP | 2011-104385 A | 6/2011 |
| WO | 03/098268 A1 | 11/2003 |
| WO | 2007/123147 A1 | 1/2007 |
| WO | 2007/041267 A2 | 4/2007 |
| WO | 2009/063435 A1 | 5/2009 |
| WO | 2010/147064 A1 | 12/2010 |
| WO | WO 2012059917 A1 * 5/2012 | ............. A61B 19/54 |

OTHER PUBLICATIONS

Communication dated Apr. 8, 2015 from the European Patent Office in counterpart application No. 12844573.1.
Communication dated Apr. 8, 2015 from the European Patent Office in counterpart application No. 12843321.6.
International Preliminary Report of PCT/JP2012/077524, dated May 8, 2014.
International Preliminary Report of PCT/JP2012/077523, dated May 8, 2014.
Office Action issued by Japanese Patent Office in corresponding Japanese Patent Application No. 2011519757, dated Apr. 1, 2014.
International Search Report of PCT/JP2010/059969, dated Jul. 6, 2010.
International Search Report of PCT/JP2012/077524 dated Dec. 4, 2012.
Communication from the United States Patent and Trademark Office dated Feb. 29, 2016 in U.S. Appl. No. 14/353,688.
Communication dated Jan. 10, 2017, from the Japanese Patent Office in counterpart Japanese application No. 2016-039320.

* cited by examiner

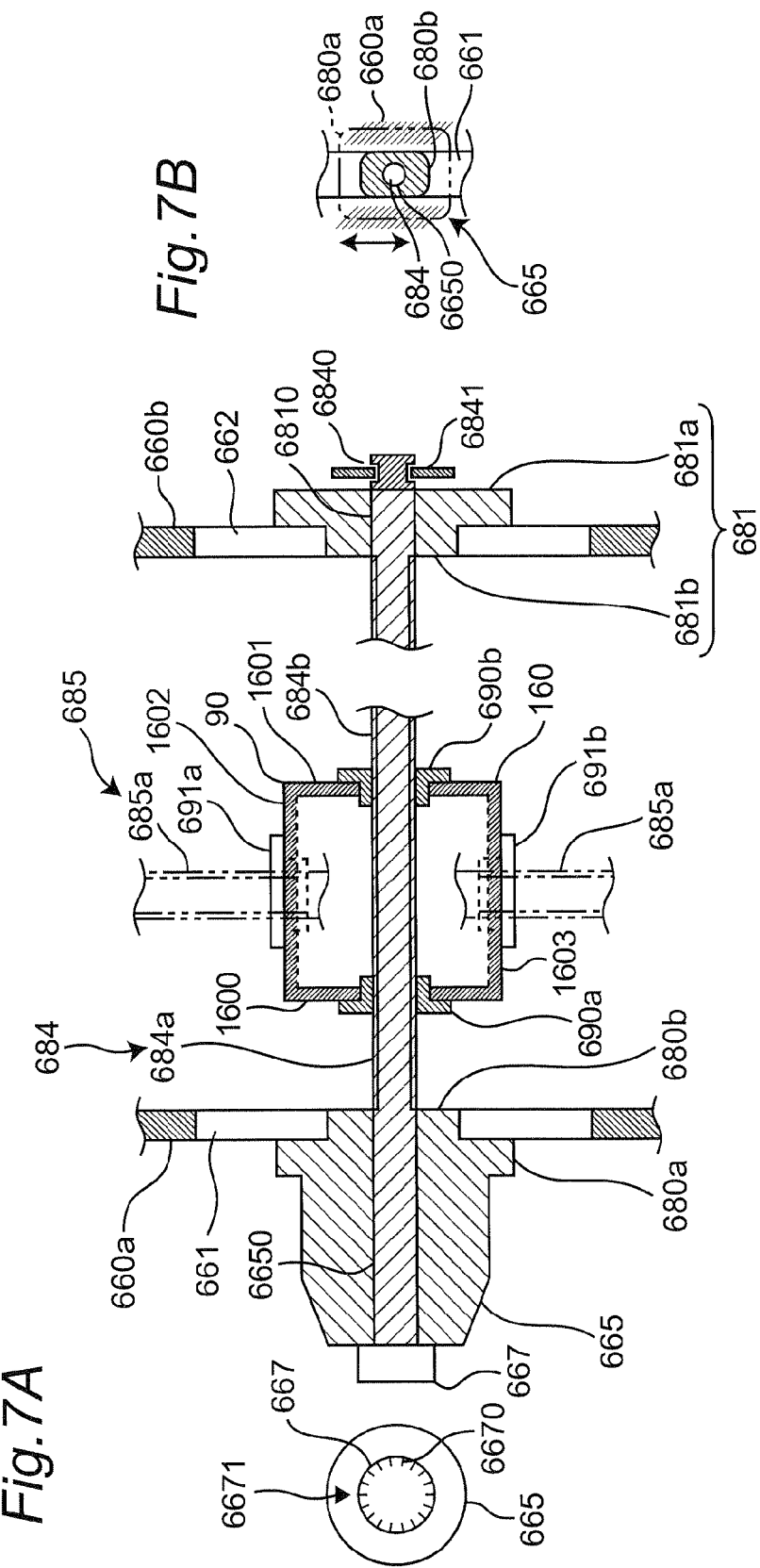
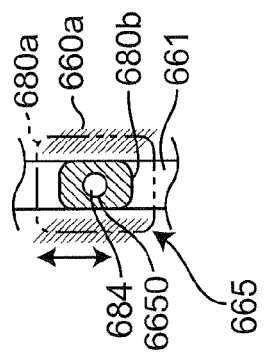
Fig.7A
Fig.7B

TRANSCRANIAL MAGNETIC STIMULATION SYSTEM

CROSS REFERENCE TO RELATED APPLICATIONS

This application is a National Stage of International Application No. PCT/JP2012/077524 filed Oct. 24, 2012, claiming priority based on Japanese Patent Application No. 2011-232883, filed Oct. 24, 2011, the contents of all of which are incorporated herein by reference in their entirety.

TECHNICAL FIELD

The present invention relates to a transcranial magnetic stimulation system for applying magnetic stimulation to specific head parts of patients.

BACKGROUND OF THE INVENTION

Recently, an enhanced interest has been paid to the transcranial magnetic stimulation therapy for treating neurological patients for which drug treatments are not necessarily effective. The transcranial magnetic stimulation therapy is relatively a newly developed one which is effective in decreasing therapeutic stress of patients and/or symptoms by providing specific part of brain such as cranial nerve with magnetic stimulation generated by the magnetic field generator positioned on the scalp of the patient.

Contrary to the conventional electric stimulation method which needs craniotomy procedure and uses indwelling electrodes which might be extremely uncomfortable to the patients, the transcranial magnetic stimulation is non-invasive and less stressful and therefore is expected to be widely used.

Patent Literature 1 discloses a specific transcranial magnetic stimulation method for applying electric current to a coil mounted on or above the scalp of patient to generate local weak magnetic pulses, causing intracranical eddy current by electromagnetic induction to apply magnetic stimulation against the nerve cells in brain underneath the coil.

Patent Literature 1 also discloses that the transcranial magnetic stimulation method effectively relieves an intractable neuropathic pain and a suitable positioning of the local stimulation results in an increased pain-relief effect. It also discloses that the most effective stimulation point slightly varies from person to person.

This means that, an achievement of an increased therapy effect highly depends on how the optimum stimulation site is identified for each patient's head, i.e., how a precise positioning of the stimulation coil is attained on the patient's head. It is also known that the therapy effect can vary according to the orientation (posture) of the stimulation coil even if it is positioned at the same place.

Patent Literatures 2 and 3 disclose techniques for positioning the stimulation coils against the patient heads by using, for example, an optical tracking system using infrared ray. This technology has been commercially available and also used in clinical applications. Patent Literature 4 discloses another apparatus for positioning the stimulation coil against the patient heads by using a multi jointed robot.

Patent Literature 1 further discloses that the effect of the transcranial magnetic stimulation therapy persists for about several hours and does not last up to several days. This means that, to attain an increased pain reduction effect, the transcranial magnetic stimulation therapy is desired to be applied regularly at smaller intervals, preferably every day, in order to reduce pain. Also, preferably the patient can take that therapy at the his or her their home or in the neighborhood clinic in which his or her regular doctor is working with minimum physical and/or economical load.

CITATION LIST

Patent Literature

[Patent Literature 1] WO 2007/123147
[Patent Literature 2] JP 2003-180649 A
[Patent Literature 3] JP 2004-000636 A
[Patent Literature 4] 2006-320425 A

SUMMARY OF THE INVENTION

Technical Problem

Each of conventional transcranial magnetic stimulation systems with the coil positioning device is designed so that it is operated by skilled specialized physician and used for examination and/or research purpose in the relatively large hospital and/or research institution, so that it needs complicated operation, enhanced skill, enlarged space, and elevated cost. This results in that it is generally difficult for the patient, his or her family, or home doctor who may be unfamiliar with the operation of the system and imposes an enormous financial burden on the patient or relatively small clinic or hospital. In addition, it may also be difficult for them to secure a large space for the installation of the system.

For the reasons above, the patient has no other choice but to go to the hospital with the transcranial magnetic stimulation and skilled physicians whenever he or she wants to undergo the transcranial magnetic stimulation therapy or to be admitted to such hospital, which practically results in that the patients have been forced to bear various burdens to take that therapy continuously.

Accordingly, the present invention is to provide a compact and economical transcranial magnetic stimulation system which is capable of providing a transcranial magnetic stimulation therapy routinely and continuously at patient's home or neighborhood home clinic without skill.

Solution to Problem

The transcranial magnetic stimulation system of the invention comprises means for generating magnetic field, the magnetic field generating means having a coil for generating a variable magnetic field to be applied to a certain part of patient's head and a holder for holding the coil; and means for recognizing a predetermined reference marking made of a specific portion of ear of the patient;

the magnetic field generating means and the recognizing means being designed so that an alignment of the recognizing means with the marking causes the coil to be set in a proper posture with respect to the certain part of the patient's head.

With the arrangement, the magnetic field generating means can be positioned with respect to the reference marking of a specific portion the patient's ear, allowing the user of the transcranial magnetic stimulation system to position the magnetic field generating means without skill which is needed for the conventional system.

Preferably, the certain portion is a tragus of the patient.

Preferably, the recognition means includes at least one imaging device provided adjacent the holder. The alignment includes aligning the optical axis with the marking. This allows that the coil is positioned in the proper posture with respect to the specific part of the patient.

Preferably, the transcranial magnetic stimulation system further comprises an optical device capable of emitting a directional beam, the optical device being provided adjacent the imaging device, wherein the alignment includes aligning an intersection of the optical axis of the optical device with the marking. This allows that the coil is positioned in the proper posture with respect to the specific part of the patient.

More preferably, the transcranial magnetic stimulation system further comprises a moving mechanism for moving the holder on and along a surface of the patient's head; and a controlling means for controlling the moving mechanism in accordance with an output from the recognition means to automatically position the holder with respect against the marking.

Advantageous Effects of Invention

According to the invention, the patient can perform the transcranial magnetic stimulation therapy routinely and repeatedly in his or her house or a neighborhood primary-care medical facility, and a more compact and economical transcranial magnetic stimulation system can be provided. The system can be operated easily by the patient, his or her family, or neighborhood primary-care doctor or assistance even though they are not experts of this system. Also, comparing the conventional space-occupying and costly system, the invention is less expensive and occupies less space so that it can be installed in a private patient's house or relatively small office or clinic.

BRIEF DESCRIPTION OF THE DRAWINGS

FIGS. 7A and 7B is a view showing a recognition unit of the transcranial magnetic stimulation system according to the third embodiment of the invention;

PREFERRED EMBODIMENT OF THE INVENTION

Referring to the accompanying drawings, an exemplary embodiment of the transcranial magnetic stimulation system according to the invention will be described below. In the following descriptions, the discussions are made to the the transcranial magnetic stimulation system which is preferably used for medical treatment in the departments of neurosurgery and neurology; however, it may be applied similarly to the medical treatment in other departments of, such as, psychosomatic and psychiatry for treating patient suffering from depression.

Although direction- and position-related terminologies such as upper and lower surfaces are used for the better understanding of the invention in the following descriptions, a technical scope of the invention should not be restrictively construed by the meanings of those terms. Also, the following descriptions relate to the specific embodiment of the invention and do not intend to limit its application.

In the following descriptions, a "posture of stimulation coil" means an orientation of the stimulation and the orientation angle of the stimulation coil, an "orientation of coil" an orientation of coil with respect to a patient's scalp, and an "angle of stimulation coil" an angle between a normal line from the patient's scalp and a direction of magnetic field.

Figure 1:
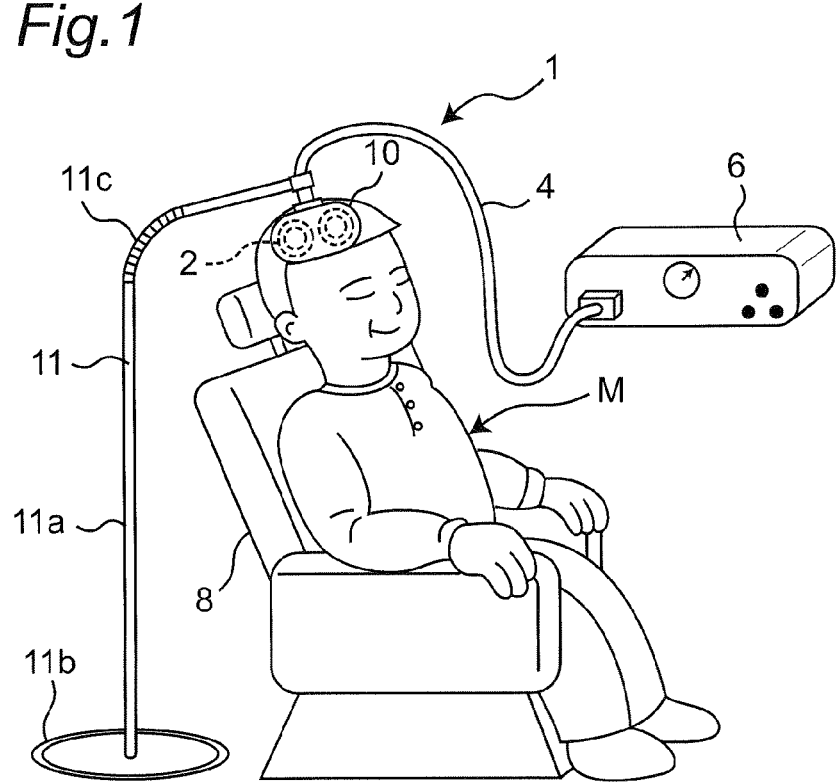
FIG. 1 is a schematic view showing a general construction of a transcranial magnetic stimulation system of the invention.

As shown in FIG. 1, the transcranial magnetic stimulation system (hereinafter referred to as "magnetic stimulation system", generally indicated at 1, includes a stimulation coil (magnetic field generating means) 2 and a magnetic stimulation control unit 6 electrically connected to the stimulation coil 2 through a cable 4. The magnetic stimulation system 1 is designed to treat and/or ease certain symptoms by applying magnetic stimulation with certain intensity into the cranial nerve of the patient M by means of the stimulation coil 2 positioned on the scalp of the patient M sitting on a seat 8 for treatment.

As shown in the drawing, a coil holder 10 holding the coil 2 is secured at a distal end of a holder fixture (posture holding means) 11. The holder fixture 11 includes a standing pole 11a and a base 11b. A part of the standing pole 11a, adjacent the distal end of the holder fixture 11, is made of a metallic flexible tube 11c, allowing the coil 2 to be positioned in an optimal way simply by holding and moving the coil holder 10 onto a predetermined position on of the scalp of the patient M. The positioning of the stimulation coil 2 against the scalp of the patient M will be described later.

The stimulation coil 2 is designed so that it can generate variable magnetic field which applies the magnetic stimulation onto at least specific positions of the patient M. Various types of conventional magnetic coils are available for the stimulation coil 2. In this embodiment, the stimulation coil 2 is a so called figure-eight coil having a configuration made by placing two spiral coils on the same plane in the form of number eight. This allows that an application of electric current to this figure-eight coil in the same direction as shown in the drawing, for example, generates the maximum inductive current density beneath the overlapped portions of the spirals. Although this stimulation coil or magnetic coil 2 may be relatively difficult to be held in a desired posture, it is advantageous to concentrate the magnetic stimulation in a certain site.

Figure 3:
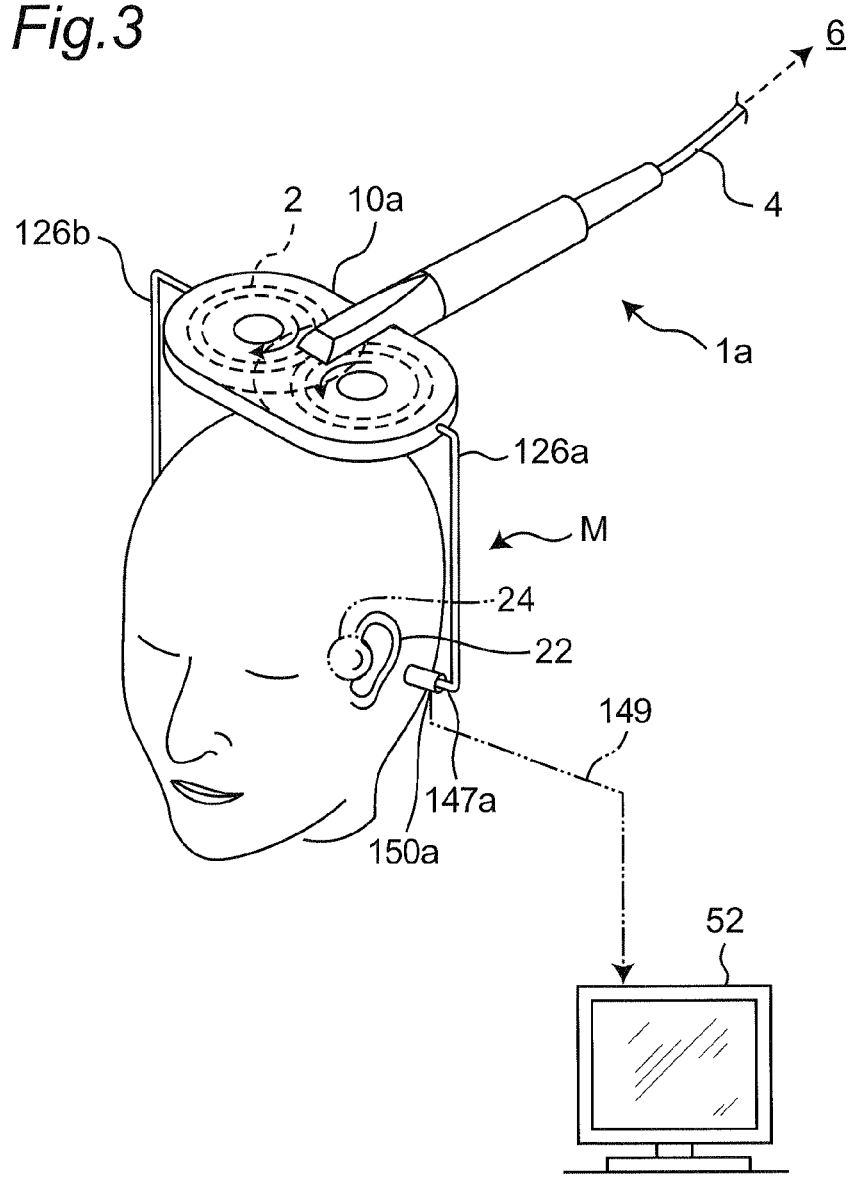
FIG. 3 is a perspective view showing the transcranial magnetic stimulation system according to the first embodiment of the invention.

As shown in FIGS. 1 and 3, the stimulation coil 2 is assembled in the coil holder 10 in the form of oval. Specifically, the coil holder 10 is made by molding non-magnetic resin material and the stimulation coil 2 is integrally formed with the coil holder 10 at the molding of the coil holder. Preferably, the bottom surface of the coil holder, facing the scalp of the patient M, has a concave spherical surface formed therewith, corresponding to an outer configuration of the head of the patient M. This allows that the coil holder 10 to be moved smoothly on the head surface 20 of the patient M. It should be noted that the planar configuration of the coil holder 10 may have oval, ellipsoidal or egg-shaped configuration such as oval.

The magnetic stimulation control unit 6, which is designed to control an application of electric current pulses to the stimulation coil 2, may use any one of conventional units. The control unit 6 is operated by an operator. In the operation, the operator can control various settings such as magnitude and/or waveform of the current pulses determining the intensity of magnetic stimulation and/or the stimulation cycle or interval.

As described in the background, an enhanced pain reduction effect can be obtained by properly concentrating and locally applying the magnetic stimulation from the coil provided on the patient's scalp on the targeted cranial nerve thereunderneath. Therefore, the optimum coil position and posture for each patient where the maximum neuropathic-pain reduction effect would be obtained by the application of magnetic stimulation is determined at the time of initial diagnostic test by using a dedicated positioning device including a coil unit similar to the coil holder 10 in the medical institution. Through this test, an object or marking for positioning is attached or formed on the body part of the patient, which is difficult to move, in order for allowing the optimum coil position and posture to be reproduced in the subsequent therapy.

Preferably, the marking is provided at a different location away from the optimum coil position so that it can be viewed directly or indirectly to recognize that the coil holder 10 is properly positioned on the head with respect to the marking. At least one marking is provided. For the purpose of precise positioning, a plurality of markings are preferably provided.

Figure 2:
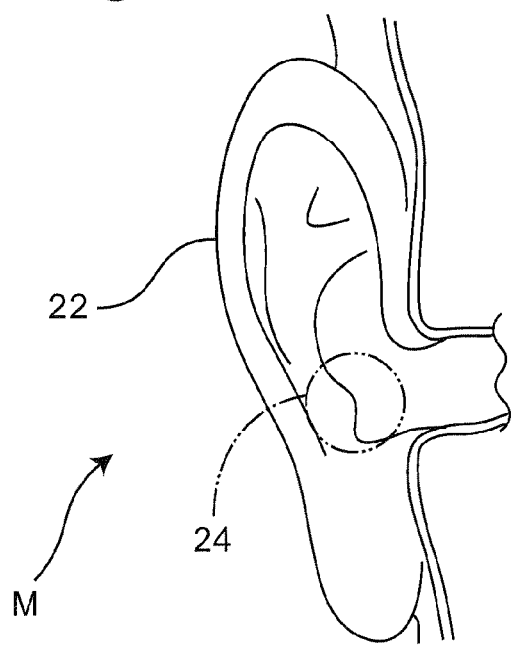
FIG. 2 is a view showing a tragus of patient which is used as a marking.

As shown in FIG. 2, the tragus 24 of the patient M is most preferably used as the marking. The earlobe or the antitragus above the earlobe may be used instead.

Descriptions will be made to embodiments of the magnetic stimulation system 1, allowing the marking or markings on the patient's tragus to be recognized easily and then the system to be positioned properly with respect to the marking or markings without difficulty.

First Embodiment

FIG. 3 shows a coil holder 10a which is configured to be capable of being positioned to the patient's tragi 24. As shown, the coil holder 10a has a pair of arm members 126a and 126b made of metal rod and supported at opposite ends thereof on the longitudinal axis extending in parallel to a line connecting the centers of the coils. The arm members 126a and 126b are extended outwardly from the opposite ends of the coil holder 10a and then bent several times into substantially a bracket form. The distal ends 147a and another (not shown) of the arm members 126a and 126b support ultracompact cameras 150a and another (not shown), respectively, with their optical axes directed substantially parallel to the upper and lower surfaces of the coil holder 10a. The optimum coil position is determined for the patient by using a coil holder which is the same as the coil holder 10a in the original diagnosis at the hospital and the cameras 150a and other are positioned to oppose the patient's left and right tragi 24 upon placement of the coil at the optimum coil position. The cameras 150a and other are connected through a communication cable 149 to a display 52 so that image signals are transmitted from the cameras 150a and other into the display where the captured images are shown on the display 52.

In operation of the magnetic stimulation system 1a of this embodiment, the patient or his or her helper conducts a positioning operation to align the collimation marks (not shown) of the cameras 150a and another (not shown) on the respective tragi 24 while viewing the display 52. The alignment of the collimation marks of the cameras 150a and other on respective tragi 24 ensures that the coil holder 10a is placed at the optimum coil position. As above, according to this embodiment, the use of the displacement between the collimation mark of the camera 150a and other and the tragus 24 ensures the patient M or his or her helper to precisely position the coil holder 10a at the optimum coil position while viewing the displacement on the display 52. Also, the patient M does not need to bear any marking such as pattern or attachment on his or her body, minimizing the stress he or she might experience. In this embodiment, the collimation mark is not limited to cross hairs and it may be circular or rectangular pattern, for example. When the collimation mark is made of cross hairs, an intersection of the horizontal and vertical lines coincides with the optical axis of the camera. When the collimation mark is made of the circular or rectangular pattern, a center of the mark coincides preferably with the optical axis of the camera. These arrangements are likewise applied to other embodiments which will be described below.

Second Embodiment

Figure 4:
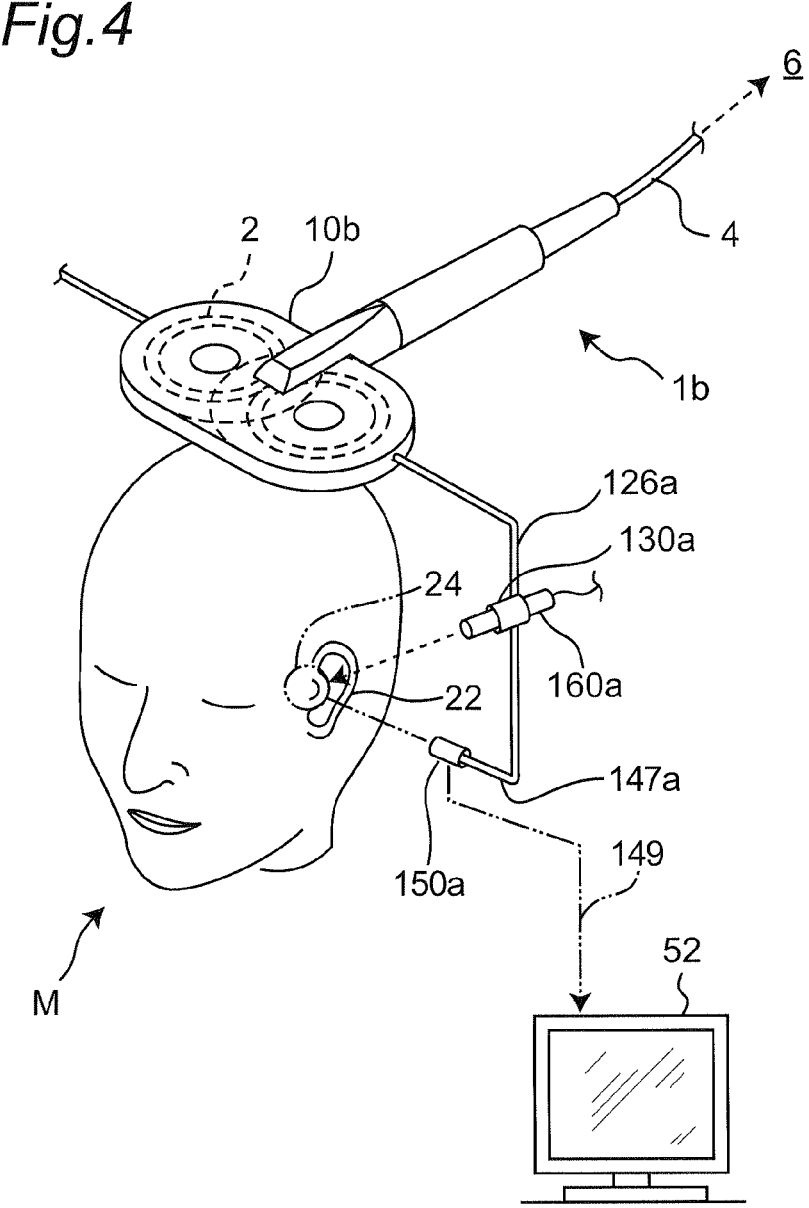
FIG. 4 is a perspective view showing the transcranial magnetic stimulation system according to the second embodiment of the invention.

FIG. 4 shows a magnetic stimulation system 1b according to the second embodiment of the invention. In this embodiment, the coil holder 10b has a pair of arm members 126a and 126b (as in FIG. 3) made of metal rod and supported at opposite ends thereof on the longitudinal axis extending in parallel to a line connecting the centers of the coils. The arm members 126a and 126b are extended outward from the opposite ends of the coil holder 10b and then bent several times into substantially a bracket form. The distal ends 147a and another (not shown) of the arm members 126a support ultracompact cameras 150a and another (not shown), respectively, with their optical axes directed substantially parallel to the upper and lower surfaces of the coil holder 10b. The bracket-like arm members 126a and other have vertical portions where optical devices such as laser beam oscillators 160a and another (not shown) are fixedly secured to the fixing member 130 with their optical axes tilted at a certain angle with respect to the upper and lower surfaces of the coil holder 10b.

Similar to the first embodiment, the cameras 150a and other are connected to the display 52 through a communication cable 149 so that images captured by the cameras 150a and other are shown on the display 52 by using image signal transmitted from the cameras 150a and other.

Figure 5A:
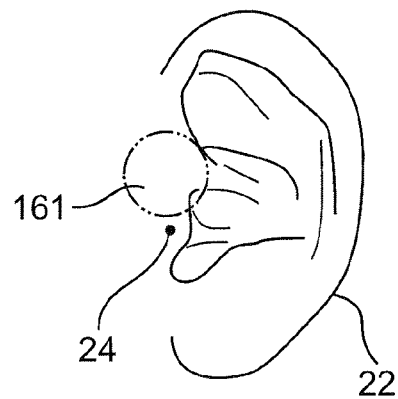
FIGS. 5A-5C are views showing a positioning of the transcranial magnetic stimulation system according to the second embodiment of the invention.
Figure 5B:
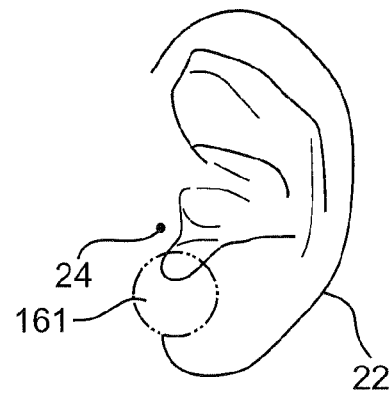
Figure 5C:
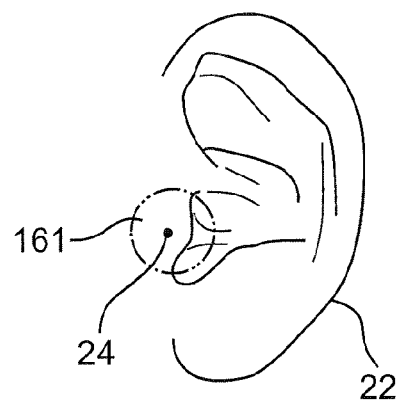

In use operation of the magnetic stimulation system 1b, the coil holder 10b is positioned adjacent its optimum coil position. In this condition, the patient or his or helper moves the coil holder 10b so that the laser spots 161 from the laser beam oscillators 160a and other are positioned on respective tragi 24 while viewing images on the display 52 captured by the cameras 150a and other. For example, as shown in FIGS. 5A and 5B, if the coil holder 10b is moved away from or toward the optimum coil position, the laser spot 161 from the laser beam oscillators 160a and other take a position lower or higher than the corresponding tragi 24. Then, the patient or the helper moves the coil holder 10b toward or away from the head surface 20 of the patient M so that the laser spots 161 of the laser beam oscillators 160a and other align with the corresponding tragi 24 (See FIG. 5C) while viewing the images on the display 52 captured by the cameras 150a and other. The proper alignment of the laser spots 161 of the laser beam oscillators 160a and other on the corresponding tragi 24 results in that the coil holder 10b is positioned at the optimum coil position. As described above, according to the second embodiment, the patient or the helper can position the coil holder 10b in a precise manner while viewing the images of the display 52 by the use of the cameras 150a and other, the laser beam oscillators 160a and other, and the displacements between the laser spots and the corresponding tragi 24.

Although the laser beam oscillator 160a and other are used as an example of optical device in this embodiment, other devices capable of emitting directional light may be used instead. Rather than light emitting diode LED, other optical device may be used which employs a light source for emitting diffusion light and a lens unit positioned ahead of the light source for forming the diffusion light from the light source into directional light.

Third Embodiment

Figure 6:
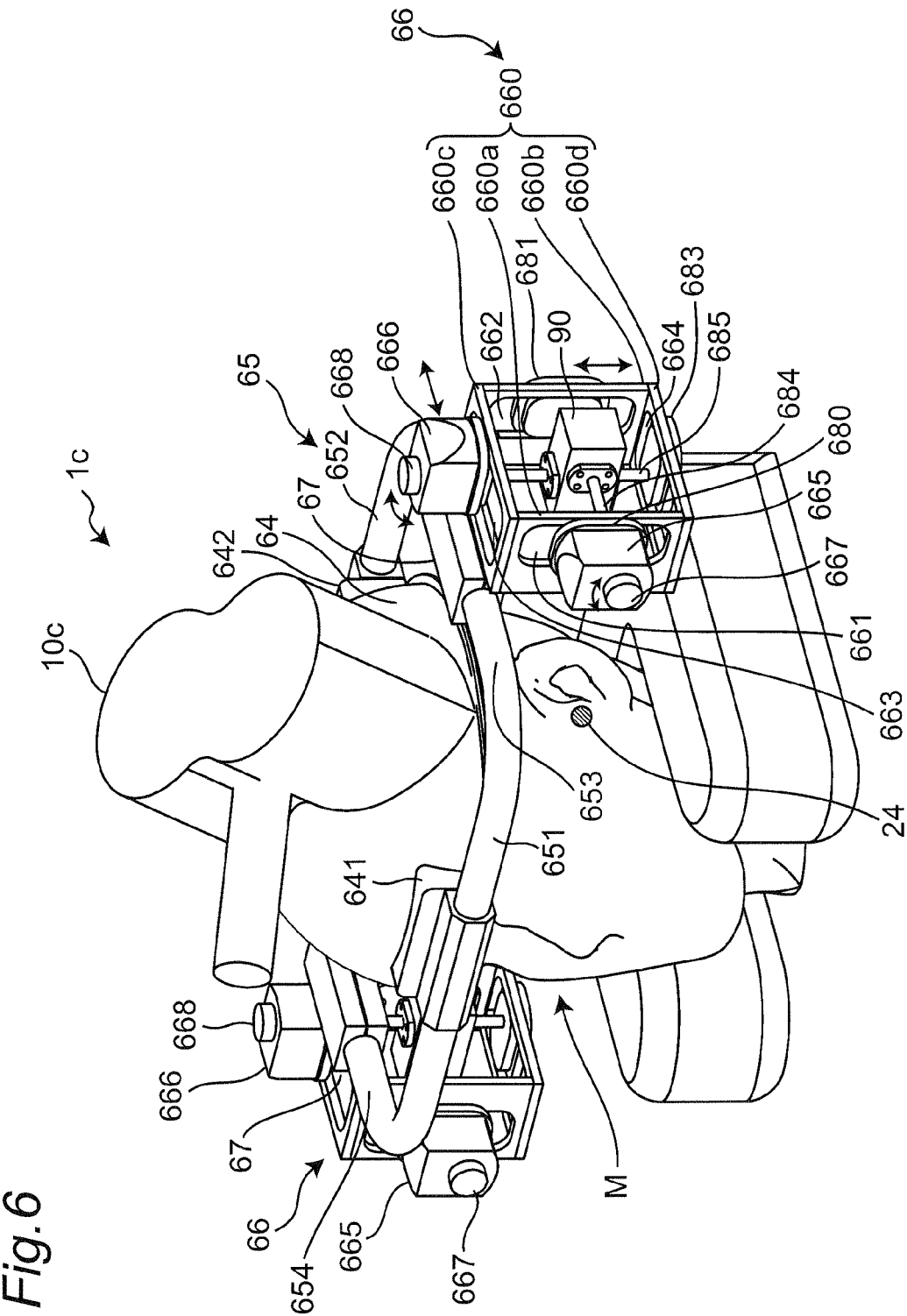
FIG. 6 is a perspective view showing the transcranial magnetic stimulation system according to the third embodiment of the invention.

FIG. 6 shows a magnetic stimulation system 1c. The magnetic stimulation system 1c has a helmet 64 having an internal configuration similar to the outline of the head surface 20 of the patient M (see FIG. 2 for example). Preferably, the helmet 64 is made of non-magnetic polymer material. The coil holder 10c with the stimulation coil (not shown) is assembled in the helmet 64. The position of the coil holder 10c relative to the helmet 64 is determined so that the coil holder 10c takes the optimum coil position or its neighborhood when the patient M wears the helmet 64.

The magnetic stimulation system 1c has a horizontal frame 65 surrounding the helmet 64. The horizontal frame 65 includes frame portions 651, 652, 653, and 654 positioned on front, rear, left and right sides of the helmet 64. In the modification, the front and rear frame portions 651 and 652 are fixed to the helmet 64 by fixing members 641 and 642. Similar to or in addition to the front and rear frame portions 651 and 652, the left and right frame portions 653 and 654 may be fixed to the helmet 64.

Figure 8:
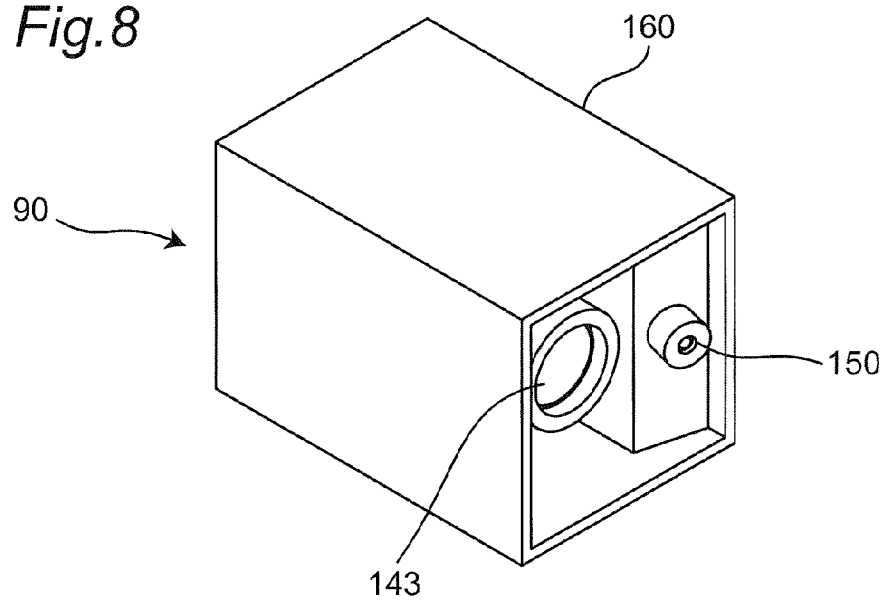
FIG. 8 is a view showing a recognition unit of the transcranial magnetic stimulation system according to the third embodiment of the invention.

Each of the left and right frame portions 653 and 654 supports means for marking recognition or a recognition unit 90. The marking recognition unit 90 includes a box-like housing 160 shown in FIG. 8 for accommodating a camera 143 for imaging the tragus 24, for example, and a light source made of laser beam oscillator 150 for emitting light ray in a direction obliquely crossing the optical axis of the camera in order to establish a suitable distance between the camera 143 and the marking. The housing 160 so constructed is supported by an adjustment mechanism 66 with openings for the camera 143 and the laser beam oscillator 150 exposed to the patient.

The adjustment mechanism 66 is fixed to the horizontal frame 65 by fixing members 67. In the modification shown, the adjustment mechanism 66 has a rectangular frame 660 including front and rear vertical frame portions 660a and 660b and upper and lower horizontal frame portions 660c and 660d. The vertical frame portions 660a and 660b and the horizontal frame portions 660c and 660d have guide slots 661, 662, 663, and 664, respectively. The guide slots 661, 662, 663, and 664 have slide blocks 665, 681, 666, and 683 fitted therein so that they move along the guide slots 661, 662, 663, and 664, respectively. FIGS. 7A-7C shows a partial enlarged view of the adjustment mechanism 66, in which the slide block 665 is indicated to have a main portion 680a and an engagement portion 680b. As shown in FIG. 7B, the main portion 680a has a width larger than that of the guide slot and the engagement portion 680b has substantially the same width as that of the guide slot, allowing the slide block 665 to move in the longitudinal direction of the guide slot 661 with the engagement portion 680b inserted in the guide slot 661. Likewise, the slide block 681 of the opposing right vertical frame portion 660b has a main portion 681a and an engagement portion 681b. The engagement portion 681b has substantially the same width as the guide slot 662, allowing the slide block 681 to move in the longitudinal direction along the guide slot 662 with the engagement portion 681b inserted in the guide slot 662. Although detailed descriptions will not be made, the slide blocks 682 and 683 associated with the upper and lower frame portions 660c and 660d have the same structure so that they can move in the respective longitudinal directions along the guide slots with the engagement portions thereof inserted in the associated guide slots.

The front and rear slide blocks 665 and 681 have through-holes 6650 and 6810 defined respective centers thereof and extending therethrough in the opposing direction, in which the cylindrical threaded shaft 684 is inserted for rotation. One end of the threaded shaft 684, e.g., a portion thereof projected from the front slide block 665, supports a knob 667 fixed thereto. The other end of the threaded shaft 684, e.g., a portion projected from the rear slide block 681, has a peripheral groove 6840 in which a C-ring 6841 is fitted. The slide blocks 682 and 683 associated with the upper and lower frame portions 660c and 660d have the same structure in each of which one end of the threaded shaft 685, e.g., a portion projected from the upper slide block, supports a knob fixed thereto and the other end of the threaded shaft 685, e.g., a portion projected from the lower slide block, has a peripheral groove in which a C-ring is fitted. This allows the paired front and rear slide blocks 665 and 681 and the paired upper and lower slide blocks 666 and 683 to move in the vertical and front-back directions as they are guided by the associated guide slots.

Central portions of the shafts 684 and 685 extend through the housing 160 of the recognition unit 90 and have respective external threads 684a and 685a defined thereon. Four walls 1600, 1601, 1602, and 1603 of the housing 160, through which the shafts 684 and 685 extend, securely support internally threaded members 690a, 690b, 691a, and 691b, respectively. The external thread 684a of the horizontally oriented shaft 684 is threaded in the internal threads of the internally threaded members 690a and 690b mounted on the front and rear walls 1600 and 1601 of the housing 160. Also, the external thread 685a of the vertically oriented shaft 685 is threaded in the internal threads 691a and 691b in the upper and lower walls 1602 and 1603 of the housing 160.

According to the magnetic stimulation system 1c so constructed, rotating the knob 667 of the shaft 784 extending in the front-rear direction causes the recognition unit 90 to move in the front-rear direction and rotating the knob 668 of the shaft 684 extending in the vertical direction causes the recognition unit 90 to move in the vertical direction, which in turn causes the camera 143 and the laser beam oscillator 150 of the recognition unit 90 to move in the vertical and front-rear directions. In use of the magnetic stimulation system 1c, the coil holder 10c is moved relative to the patient M wearing the helmet 64 into the optimum coil position of the patient M. Once positioned at the optimum coil position, the coil holder 10c is secured to the helmet 64. Then, the patient or helper rotates the knobs 667 and 668 to move the recognition unit 90 so that the optical axis of the laser beam oscillator 150 is oriented to the target mounted on the patient M, e.g., the laser spot 161 is mounted on the tragus 24 of the patient M while viewing the images on the display (not shown).

After the camera 143 and the laser beam oscillator 150 are set at respective positions corresponding to the optimum coil position, the coil holder 10c is readily positioned at the optimum coil position simply by aligning the optical axis of the laser beam oscillator 150 on the target in the subsequent wearing of the helmet 64. Preferably, as shown in FIG. 7A the knob 667 has a scale marked on its peripheral surface and the slide block 665 adjacent the knob 6670 has a reference 6671 marked thereon, allowing the knob to be set into a position corresponding to the optimum coil position. Although the recognition unit 90 is designed to be moved in the vertical and front-rear directions with respect to the head of the patient M in the modification, it may be designed to rotate about horizontal and vertical axes. Also, the camera 143 and the laser beam oscillator 150 may be designed so that their positions are independently adjusted.

According to the magnetic stimulation system in the first to third embodiments the coil holder 10 is moved and positioned on the patient's head surface by the patient M or the helper; however, this positioning procedures may be automated by a magnetic stimulation system equipped with a moving device or mechanism which will be described below.

Fourth Embodiment

Figure 9:
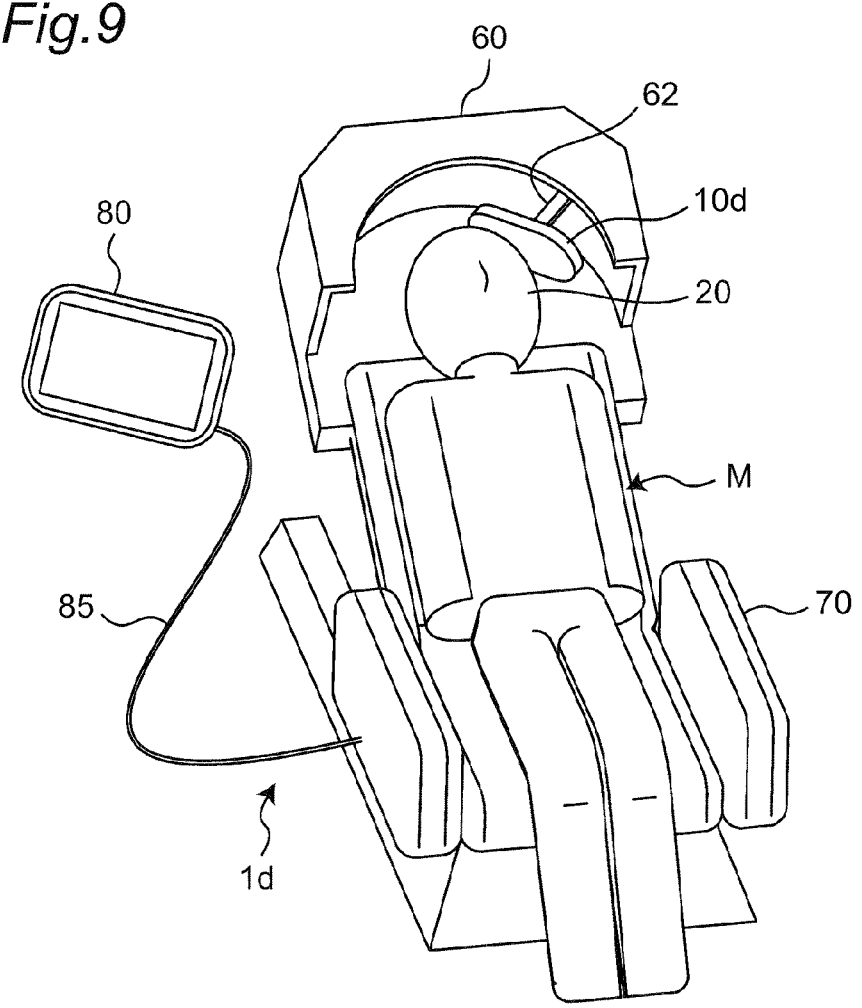
FIG. 9 is a perspective view showing a general construction of the transcranial magnetic stimulation system according to the fourth embodiment of the invention.

FIG. 9 shows the magnetic stimulation system 1d equipped with the moving device 60 or mechanism which is designed to move the coil holder 10d with the stimulation coil (not shown) along a spherical surface resembling the head surface 20 of patient M. The coil holder 10d is supported by a support member 62 which is capable of supporting it in a desired posture against the head surface 20 of patient M. The moving device 60 is positioned above the head of patient M so that it covers a part of the head of patient M. In the drawing, a medical chair 70 on which patient M lies on his or her back supports the moving device 60 which is electrically connected to a controller 80 or controlling means for controlling the moving device 60 through a cable 85. Further, although not shown the coil holder 10d supports on its bottom surface an image sensor or recognition means for automatically detecting the marking provide on the head surface 20 of patient M.

With the magnetic stimulation system 1d so constructed, the image sensor automatically recognizes the marking as it moves along the head surface of patient M and thereby positions the coil 2 of the coil holder 10d at the optimum coil position.

According to the magnetic stimulation system of the embodiments 1-4, the stimulation coil can be positioned at the optimum coil position by positioning the coil holder against the patient tragus 24 (marking), allowing users such as patient M and helper to position the coil holder or coil without difficulty without skill.

1: transcranial magnetic stimulation system
2: stimulation coil
4: cable
6: magnetic stimulation controller
8, 70: chair
10: coil holder
22: patient's ear
24: patient's tragus
50: converter
52: display
60: moving device
150a: camera
160a: laser beam oscillator
M: patient

The invention claimed is:

1. A transcranial magnetic stimulation system, comprising:
    magnetic field generating means configured to generate a variable magnetic field to be applied to a certain part of a patient's head, the magnetic field generating means comprising a coil and a coil holder holding the coil; and
    recognizing means configured to recognize a specific portion of an ear of the patient as a predetermined reference, wherein
    the magnetic field generating means and the recognizing means are connected with each other and are configured such that aligning an optical axis of the recognizing means to intersect the predetermined reference simultaneously aligns the magnetic field generating means in a predetermined posture with respect to the certain part of the patient's head.

2. The transcranial magnetic stimulation system of claim 1, wherein the specific portion is a tragus of the ear of the patient.

3. The transcranial magnetic stimulation system of claim 1,
    wherein the recognizing means further comprises at least one imaging device.

4. The transcranial magnetic stimulation system of claim 3, wherein the recognizing means further comprises an image signal display configured to show captured images by the imaging device.

5. The transcranial magnetic stimulation system of claim 4, wherein the recognizing means further comprises an optical device, the optical device comprising a second optical axis, the optical device configured to emit a directional beam along the second optical axis of the optical device, the optical device being located adjacent to the imaging device, the optical axis of the imaging device being configured to intersect with the second optical axis of the optical device at an intersection, wherein aligning the recognizing means with respect to the predetermined reference marking further comprises aligning the intersection of the optical axis of the optical device with the marking and setting the magnetic field generating means in the predetermined posture with respect to the certain part of the patient's head.

6. The transcranial magnetic stimulation system of claim 3, wherein,
    the recognizing means further comprises an optical device aligned along a second optical axis, and
    the recognizing means is further configured such that, in a case where the magnetic field generating means is aligned in the predetermined posture, the optical axis of the recognizing means intersects both:
        a. the second optical axis of the optical device, and
        b. the predetermined reference.

7. The transcranial magnetic stimulation system of claim 1, further comprising:
    a moving mechanism configured to move the magnetic field generating means on or above, and along a surface of the patient's head; and a controlling means configured to control the moving mechanism in accordance with an output from the recognizing means to automatically position the magnetic field generating means with respect to the predetermined reference.

8. The transcranial magnetic stimulation system of claim 1, wherein
the magnetic field generating means are further configured to, in response to a detection that the optical axis is not aligned with the predetermined reference, automatically actuate the magnetic field generating means from one position about the patient's head to another position at the predetermined posture, while the magnetic field generating means and the recognizing means are mounted to the patient's head.

9. The transcranial magnetic stimulation system of claim 1, wherein
the recognizing means further comprises a first imaging device configured to recognize a tragus as the specific portion of the ear,
the recognizing means further comprises a second imaging device, at an opposing side of the magnetic field generating means as compared to the first imaging device, configured to recognize another tragus of another ear of the patient, and
the recognizing means is further configured to determine that the magnetic field generating means is set in the predetermined posture by determining that the optical axes of the first and second imaging devices intersect respective ones of the tragus and the another tragus.

10. The transcranial magnetic stimulation system according to claim 1, wherein the magnetic field generating means and the recognizing means are attached to each other and configured such that rearranging the recognizing means with respect to the patient's head also rearranges the magnetic field generating means with respect to the patient's head.

11. The transcranial magnetic stimulation system of claim 1, wherein the magnetic field generating means comprising a coil.

12. A transcranial magnetic stimulation system, comprising:
magnetic field generating means comprising a coil, configured to generate a variable magnetic field to be applied to a certain part of a patient's head and a holder configured to hold the coil; and
recognizing means configured to recognize a specific portion of an ear of the patient as a predetermined reference, wherein
the magnetic field generating means and the recognizing means are further configured to be mounted to the patient's head by the holder, and are further configured such that aligning the recognizing means with respect to the predetermined reference sets the coil in a predetermined posture with respect to the certain part of the patient's head, wherein
the recognizing means further comprises a first imaging device configured to recognize a tragus as the specific portion of the ear,
the recognizing means further comprises a second imaging device, at an opposing side of the magnetic field generating means as compared to the first imaging device, configured to recognize another tragus of another ear of the patient, and
the recognizing means is further configured to determine that the magnetic field generating means is set in the predetermined posture by determining that the optical axes of the first and second imaging devices intersect respective ones of the tragus and the another tragus.

13. A transcranial magnetic stimulation system, comprising:
magnetic field generating means configured to generate a variable magnetic field to be applied to a certain part of a patient's head, the magnetic field generating means comprising a coil and a coil holder holding the coil; and
recognizing means configured to recognize a specific portion of an ear of the patient as a predetermined reference, wherein
the magnetic field generating means and the recognizing means are further configured to be connected with each other, and are further configured such that aligning an optical axis of the recognizing means to intersect the predetermined reference simultaneously aligns the magnetic field generating means in a predetermined posture with respect to the certain part of the patient's head, wherein
the recognizing means further comprises a first imaging device configured to recognize a tragus as the specific portion of the ear,
the recognizing means further comprises a second imaging device, at an opposing side of the magnetic field generating means as compared to the first imaging device, configured to recognize another tragus of another ear of the patient, and
the recognizing means is further configured to determine that the magnetic field generating means is set in the predetermined posture by determining that the optical axes of the first and second imaging devices intersect respective ones of the tragus and the another tragus.

14. A transcranial magnetic stimulation system, comprising:
magnetic field generating means configured to generate a variable magnetic field to be applied to a certain part of a patient's head, the magnetic field generating means comprising a coil and a coil holder holding the coil; and
recognizing means configured to recognize a specific portion of an ear of the patient as a predetermined reference, wherein
the magnetic field generating means and the recognizing means are further configured to be connected with each other such that aligning an optical axis of the recognizing means to intersect the predetermined reference simultaneously aligns the magnetic field generating means in a predetermined posture with respect to the certain part of the patient's head.

15. A transcranial magnetic stimulation system, comprising:
magnetic field generating means configured to generate a variable magnetic field to be applied to a certain part of a patient's head, the magnetic field generating means comprising a coil and a coil holder holding the coil; and
an optical device comprising an optical axis, the optical device configured to emit a directional beam along the optical axis of the optical device, and the optical device is configured such that aligning the optical axis of the optical device to intersect a predetermined reference simultaneously aligns the magnetic field generating means in a predetermined posture with respect to the certain part of the patient's heady.

16. A method for use with a transcranial magnetic stimulation system, comprising:
providing magnetic field generating means configured to generate a variable magnetic field to be applied to a certain part of a patient's head, the magnetic field generating means comprising a coil and a coil holder holding the coil; and providing recognizing means configured to recognize a specific portion of the patient as a predetermined reference, positioning the magnetic field generating means and the recognizing means comprises aligning an optical axis of the recognizing means to intersect the predetermined reference, the aligning the optical axis of the recognizing means simultaneously aligns the magnetic field generating means in a predetermined posture with respect to the certain part of the patient's head.

\* \* \* \* \*